(12) United States Patent
Portalupi

(10) Patent No.: US 10,383,706 B2
(45) Date of Patent: Aug. 20, 2019

(54) METHOD AND APPARATUS FOR ORTHODONTIC ATTACHMENT FABRICATION AND PLACEMENT

(71) Applicant: Richard Portalupi, Vacaville, CA (US)

(72) Inventor: Richard Portalupi, Vacaville, CA (US)

( * ) Notice: Subject to any disclaimer, the term of this patent is extended or adjusted under 35 U.S.C. 154(b) by 582 days.

(21) Appl. No.: 14/571,032

(22) Filed: Dec. 15, 2014

(65) Prior Publication Data

US 2016/0166357 A1     Jun. 16, 2016

(51) Int. Cl.
| A61C 7/00 | (2006.01) |
| A61C 7/14 | (2006.01) |
| A61C 7/16 | (2006.01) |

(52) U.S. Cl.
CPC ................ *A61C 7/146* (2013.01); *A61C 7/16* (2013.01)

(58) Field of Classification Search
CPC .................................. A61C 7/146; A61C 7/16
See application file for complete search history.

(56) References Cited

U.S. PATENT DOCUMENTS

| 6,250,918 | B1 | 6/2001 | Sachdeva et al. |
| 7,020,963 | B2 | 4/2006 | Cleary et al. |
| 7,188,421 | B2 | 3/2007 | Cleary et al. |
| 7,476,100 | B2 | 1/2009 | Kuo |
| 7,585,172 | B2 | 9/2009 | Rubbert et al. |
| 7,845,938 | B2 | 12/2010 | Kim et al. |
| 2005/0074716 | A1 | 4/2005 | Cleary et al. |
| 2005/0227196 | A1* | 10/2005 | Von Mandach ....... A61C 7/146 433/9 |
| 2005/0239013 | A1* | 10/2005 | Sachdeva ............... A61C 7/146 433/24 |
| 2007/0031774 | A1* | 2/2007 | Cinader, Jr. ............. A61C 7/00 433/24 |
| 2007/0031791 | A1* | 2/2007 | Cinader, Jr. ........... A61C 7/146 433/213 |
| 2010/0138025 | A1 | 6/2010 | Morton et al. |
| 2011/0020761 | A1 | 1/2011 | Kalili |
| 2012/0150494 | A1 | 6/2012 | Anderson et al. |

* cited by examiner

*Primary Examiner* — Nicholas D Lucchesi
(74) *Attorney, Agent, or Firm* — Pamela Winston Bertani

(57) ABSTRACT

The invention is a method and apparatus for placing prefabricated orthodontic attachments (i.e. purchase and retention points) with precision and reliability. The invention incorporates the use of one or more prefabricated attachment shapes, each employed in conjunction with a corresponding retention register, etching stencil having an etchant limiting dam, and attachment delivery tray having a soft inner shell and rigid outer shell to ensure accurate attachment delivery. The disclosed invention will result in more accurate tooth movement and less excess bonding plastic (i.e., flash) on patent teeth after attachment placement, which will result in more desirable patient outcomes.

30 Claims, 11 Drawing Sheets

METHOD AND APPARATUS FOR ORTHODONTIC ATTACHMENT FABRICATION AND PLACEMENT

FIELD OF THE INVENTION

This invention relates to the art and science of tooth movement, orthodontic biomechanics and dental orthopedics. More specifically, the invention relates to an apparatus and method of fabricating and placing orthodontic attachments onto human teeth in the use of clear, plastic aligners for teeth.

BACKGROUND

The art and science of aligning teeth and modifying the growth and form of the human face, known as orthodontics, is a centuries old practice. Over the decades, continuous discourse and controversy have circulated among orthodontic practitioners, scientists and researchers regarding the movement and extraction of human teeth. In 1901 orthodontic pioneer Edward Angle lead the industry in advocating an uncompromising position staunchly against the extraction of teeth to alleviate dental crowding, malalignment, or bite related (i.e., occlusal) problems. Conversely, Calvin Case and others in the industry at that time were vocal proponents of tooth extraction therapy. Heated debate regarding the pros and cons of tooth extractions as a treatment strategy continues vigorously to this day.

As time passed, and the use of tooth extraction therapy proliferated in the industry during the early and mid-1900s, practitioners began documenting orthodontic extraction cases that culminated in compromised patient profiles, highlighted by patients demonstrating insufficient lip support for optimal facial aesthetics. Consequently, the practitioners' pendulum began to swing back toward Dr. Angle's practice philosophy against the use of tooth extraction therapy as a primary strategy to address patient occlusal scenarios. Practitioners and other industry participants began employing a more thoughtful approach to diagnostic and treatment planning involving tooth extraction therapy.

The gradual decline in employing tooth extraction strategies coincided with increased practitioner efforts to identify innovative appliances capable of moving, as opposed to extracting, human teeth. Many tooth movement appliances at this time were attached to teeth surfaces and various forms of force were applied to the attached appliances in order to effectuate desired movement. Conventional sources of force involved the use of springs and wires to apply force to dental appliances attached to a patient's teeth. Of interest to aligner technology is the use of rubberized teeth aligners, commencing in the late 1800s, made from a material called vulcanite, which was formed over plaster teeth models and subsequently delivered to the patient's dentition to cause desired tooth movement.

In 1942, an apparatus called the Edgewise appliance was introduced into the marketplace. This appliance incorporated stainless steel brackets with milled rectangular edgewise slots to house orthodontic wires. These brackets were welded to stainless steel bands that were then cemented onto a patient's teeth. In the 1970s, several key publications and new dental appliances emerged disclosing tooth movement techniques that ultimately became industry standards in the field of Orthodontic Biomechanics. One such appliance was the Straight Wire Appliance, which incorporated specific angles milled into bracket slots so that rectangular shaped wires could better control the movement of teeth in all three planes of space without having to bend a stainless steel wire at each tooth. This technology was considered by many as a significant orthodontic innovation.

Also during the 1970s, several leading practitioners became increasingly dissatisfied with the finished results of patient cases involving the use of tooth movement technology available at the time. Practitioner dissatisfaction derived from the belief that patient occlusion or bite could be related to symptoms of jaw joint disorder, which practitioners increasingly encountered in the clinical presentation of orthodontic patient cases. These practitioners turned to their dental colleagues in the field of restorative dentistry, who treated patient occlusions with more precision in coordination with jaw muscles and the temporomandibular (jaw) joints (TMJ").

Subsequently, new systems and refinements of Straight Wire Appliances emerged, which were capable of achieving tooth movement with more precision and predictability. The development of these new technologies is significant because the proponents of these new techniques were early critics of the use of clear plastic aligners to achieve tooth movement. The proponents believed that, while clear plastic aligner appliances may improve teeth alignment, such aligners lacked the capacity to position teeth with the level of precision required to achieve the best and most reliable patient outcomes.

In the late 1970s, an orthodontic treatment philosophy known as Goal Centered Treatment was published and became prevalent in the Orthodontic Biomechanics industry. This philosophy guides practitioners to utilize 7 specific goals in diagnosing and establishing treatment plans for each individual orthodontic case. The 7 specific orthodontic goals are summarized below:

(1) Dental Esthetics: Nicely aligned teeth and a beautiful smile;

(2) Facial Esthetics: A pleasant looking face, where from a profile view the forehead, nose, lips and chin are balanced, and from a frontal view facial symmetry is achieved;

(3) Functional Occlusion: (A) A healthy bite that masticates food comfortably and efficiently, and that will contribute to the longevity of the supporting periodontal (gum) tissues and to dental enamel integrity with regard to wear; (B) Key points of functional occlusion incorporate cuspid rise and anterior guidance whereby cuspids and incisors lift off of the posterior teeth so that stress is taken off of chewing muscles and TMJ joint hard and soft tissue; (C) Minimization of closing prematurities, which are contacts of the teeth during the arc of closure of the jaw initiated in the centered position of the jaw joint (Centric Relation) that lead to distraction of the jaw from the joint as it is translated to the most interdigitated position of the teeth (Centric Occlusion). Many clinicians believe that these movements, commonly referred to as CR/CO slides, are related to TMJ Disorders and jaw joint pain;

(4) Periodontal (Gum Tissue) Health: Over expansion of dental arches may lead to gum tissue recession and exposure of teeth roots;

(5) Healthy Jaw Joint (TMJ): A bite that functions in harmony with the jaw joint and supporting muscles and ligaments;

(6) Stability: Lasting results that are sustainable over time; and (7) Addressing The Patient's Chief Complaint: Making sure that the patient's primary treatment objectives are achieved and not overlooked or otherwise diminished during orthodontic planning.

As the field of Orthodontic Biomechanics continued to evolve into the 21$^{st}$ Century, practitioners increasingly investigated biologic considerations of tooth movement at the cellular and molecular levels in combination with the pure mechanical forces of dental appliances. Experts in the field investigated the concepts of straight line vector forces, rotational forces (or moments), centers of rotation, centers of resistance, and undesired side effects in applying forces to move teeth.

Orthodontic tooth movement historically occurred with the use of relatively heavy intermittent forces, followed by a biologic response of the patient's teeth, bone, and supporting tissues. Some patient biologic responses were harmful to patients, leading ultimately to necrosis (i.e., tissue death), loss of root integrity, and root resorption. Orthodontist typically employed a biologic repair process, via a time out or recess from treatment, and orthodontic forces were subsequently reapplied. Research conducted during the last decade has revealed that biologically healthy and efficient tooth movement usually occurs with the application of continuous forces in the range of 75 to 200 grams of continuous force.

In evaluating advances in tooth movement technology, a common challenge, that of anchorage, became a primary topic of peer review discourse and clinical research. From a clinical point of view, anchorage involves an orthodontic practitioner's attempt to stabilize (i.e., anchor) patient teeth to diminish tooth movement while applying movement forces to other teeth. Typical anchorage techniques employ headgear, heavy arch wires, trans-palatal arch wires, springs, and later miniature bone screws or temporary anchorage devices ("TADs"), and currently, aligners.

Originally, wires used in orthodontics were fabricated from gold, and then later from stainless steel. Both were useful at the time, but their biological properties had limitations. For instance, gold is relatively soft and expensive. Stainless steel wires generate forces that may exceed the biologic optimum for tooth movement, and their range of action is relatively limited. Modem metallurgy has led to various new age wires, including nickel-titanium alloys and others, which provide measurably more gentle forces over a longer period of time.

Conventional anchorage technology currently involves the use of aligner devices to achieve tooth stabilization. Indeed, the use of clear plastic aligners to move teeth is not a new concept in orthodontics. Conventional aligners have been made from thin, thermoplastic sheets that incorporate clear plastic made from a polyester, polypropenate, or similar material, which is heated to soften and then thermoplastically vacuum-pressed or positive pressure-pressed over plaster models in a dental laboratory. A series of such models were then constructed in the laboratory and reconfigured with small increments of movement of the teeth in plaster models so that a series of aligners would move the teeth in the mouth in a similar fashion. Plastic buttons, similar to conventional attachments or engagers, were used as retentive points oftentimes along with these early aligners. Thermoplastic appliances were also used in the fabrication of temporary crowns in restorative dentistry, vehicles to house dental bleaching material, retainers, athletic mouth guards, and hard splints or night guards for TMJ patients.

At this time in the industry, a clinical methodology did not exist to calculate accurately, or even remotely, the forces placed on teeth by these earlier teeth aligners. Forces were judged primarily by patient reaction upon aligner placement onto a patient's teeth, and gingival tissue blanching if forces were excessive. However, in 1997 two Stanford University MBA graduate students initiated the development of an orthodontic appliance that would revolutionize the profession. Both graduate students were previous orthodontic patients and had personally experienced conventional orthodontic treatment involving bracketed appliances. One of the graduate students noticed that when he did not wear his retainers, his teeth gradually moved, but when he put his clear thermoplastic retainers back into his mouth, his teeth quickly realigned. As a result of their direct patient experience with conventional orthodontic bracketed appliances, the graduate students subsequently worked with Silicon Valley computer programmers to develop three-dimensional imaging graphics software to move teeth virtually in stages. This imaging graphics technology was used to generate a series of aligners from physical plastic models, which included a different patient aligner for each stage of tooth movement. Following the development of this virtual tooth moving imaging graphics technology, other marketplace participants began developing similar software-generated orthodontic appliances.

By the year 2000, digital graphics software products, from various software manufacturers, were available in the marketplace. Initially, the orthodontic community did not fully embrace this imaging graphics technology and related appliances. Some practitioners reported negative experiences involving clinical use of the software and corollary orthodontic appliances. Moreover, these products were marketed directly to the public, which created a significant initial demand, but lacked adequate long-term clinical studies to identify and resolve the clinical presentation of product flaws involving various patient cases. For instance, the first generation of ceramic tooth colored brackets was initially popular in the marketplace, as their esthetic appeal was readily apparent. However, practitioners employing these first generation brackets later discovered that the appliances were also highly abrasive, causing severe enamel wear if opposing teeth came into contact with the ceramic brackets. Also, the corresponding silane-based adhesive system was too strong, leading to patient tooth fracture upon bracket removal.

In addition to the clinical presentation of imaging graphics technology product flaws, an increasing number of practitioners reported concerns regarding the future impact that these products may have on the credibility and efficacy of the practice of Orthodontic Biomechanics. Because orthodontists were initially resistant to embracing imaging graphics tooth movement technology, companies began marketing these products directly to general dentists. Consequently, a significant segment of the tooth movement market was lost to general dentist providers, producing numerous patient outcomes that were substantially less than desirable. While general practitioners were able to achieve some level of tooth movement employing imaging graphics technology, precise three-dimensional tooth positioning was commonly not achieved. A substantial number of patient cases did not meet industry standards, and imaging graphics technology suffered harsh criticism. These circumstances corroborated practitioner concerns that directly marketing imaging graphics technology products to the public could result in establishing a cookbook system for generating tooth movement, which would obviate the application of specialized orthodontic tooth movement treatment in the marketplace. The core concern was that the expertise required to achieve effective, reliable and reproducible tooth movement patient outcomes would be increasingly relegated by a cookbook tooth movement system that practically anybody could provide. Orthodontists and other experts in the field of Orthodontic Biomechanics continue to advocate the position that effective tooth movement remains both an art and a science, and those orthodontic specialists trained in achieving desired patient tooth movement outcomes are best suited to deliver such services.

Over time, a small group of noteworthy orthodontists began working closely with biomechanical engineers in the aligner systems industry to refine existing aligner systems and render them capable of moving teeth according to industry standards. The general hypothesis was that as brackets were merely tools to move teeth to specific positions in the three dimensions of space, so too could aligner system tools be refined to move teeth in a similar fashion. The key objectives in this regard were to define clearly patient goals, and correspondingly develop techniques and methodologies to achieve patient goals employing aligner systems.

To this end, prospective aligner system innovations involved the following well established three dimensional tooth movement components:

Torque is the tipping of a tooth in the buccal-labial/lingual and buccal-labial/palatal direction (cheek side/tongue side or cheek side/palate side). If the center of rotation is on the crown of the tooth, the torque is referred to as either "labial (or buccal) root torque" or if in the opposite direction "palatal (or lingual) root torque". If the center of rotation is about the root apex, the torque is referred to as crown torque. In reality, the center of rotation is usually not at either the crown or root apex and torqueing movements result in both movement of the crown and the roots, at least with bracketed appliances;

Angulation is the tipping of teeth in a mesial/distal direction (forward/backward at the contact points);

Rotation is the circular or twisting movement (a moment force) about the long axis of the root and crown of the tooth. This is the straightening of crooked teeth;

Bodily Movement is the movement of the whole tooth through bone with little or no tipping, torqueing, or rotation of the tooth. In bracketed orthodontic treatment this is accomplished with a combination of both straight line vector forces and moment (rotational) forces. In reality, true bodily movement rarely, if ever, occurs in orthodontics. Teeth move along a rigid arch wire with small tipping movements and periods of recovery;

Intrusion is the movement of teeth towards the apex of the root;

Extrusion is the movement of teeth in the opposite direction, i.e. towards the crown of the tooth; and Anchorage is the stabilization or one or more teeth to resist a reciprocal force and movement while applying a force to move other teeth.

Aligner systems have for several years used small bits of plastic or composite material bonded to teeth to help retain aligners with undercuts that act as purchase points upon which tooth movement forces are applied. The composite material components were referred to as attachments, buttons, engagers, and other similar names particular to manufacturers. Early attachment designs were usually round or ovoid in shape with rounded top surfaces. A frequently encountered problem with aligner systems employing conventional attachments is that varying tooth surfaces often provide insufficient contoured surface area onto which the attachments and corresponding aligners can adhere securely. Consequently, such aligners often cannot adhere to teeth without slipping.

In addition, a significant level of frustration exists in the marketplace regarding the fabrication, placement, and effectiveness of attachments used in conjunction with conventional aligner systems. Currently available aligner technologies do not provide a predictable, reliable system or method for precise attachment fabrication or placement. From a practitioner's point of view, it is critical for the success and efficacy of these attachments and engagers that they are precisely applied to the tooth in the same shape and form as intended, without distortion. However, current attachment placements techniques are significantly technique sensitive. Application of the attachments is often delegated to dental auxiliaries who have varying levels of skill and consistency in their technique. They may also choose whatever composite material they have available, from highly filled to lightly filled with large or small particle sizes, or unfilled altogether. The choice of material for the attachments makes a significant difference in the long-term integrity of the attachment and its fit with corresponding aligners.

Further, if either too much or too little pressure is placed on the attachment template by the clinician during fabrication, the attachment can be greatly distorted. If too much composite is placed in the attachment template, a great deal of excess composite or "flash" will result. Flash can negatively affect aligner fit, and can lead to a negative patient experience during flash removal by the clinician. Clinician attempts to shape up attachments after placement can further distort attachments, and occasionally attachments can have voids as a result of poor placement technique. All of these shortcomings in technique cause what was intended as precision attachment to become imprecise and inconsistent. In practice, attachment placement is consistently inconsistent.

The results of imprecise attachment fabrication and placement include: less efficient tooth movement due to poor engagement of the aligner tray with the attachment; more mid-course corrections and refinements; longer treatment times; lower profits for both the doctors and the aligner companies; more difficulty for patients, and therefore less positive patient experiences; and inaccurate, imprecise tooth movement outcomes.

Information relevant to attempts to address tooth movement technologies can be found in U.S. Pat. No. 7,585,172 issued to Rubbert et al. entitled Orthodontic Treatment Planning With User-Specified Simulation Of Tooth Movement; U.S. Pat. No. 7,188,421 issued to Cleary et al. entitled Orthodontic Appliances Having A Contoured Bonding Surface; U.S. Pat. No. 7,020,963 issued to Cleary et al. entitled Method And Apparatus For Indirect Bonding Of Orthodontic Appliances; U.S. Patent Application Publication No. 2012/0150494 by Anderson et al. entitled Orthodontic Aligner Fabrication By Overlay Method; U.S. Pat. No. 7,845,938 issued to Kim et al. entitled Indirect Bonding Trays For Orthodontic Treatment And Methods For Making The Same; U.S. Pat. No. 7,476,100 issued to Kuo entitled Guide Apparatus And Methods For Making Tooth Positioning Appliances; U.S. Patent Application Publication No. 2010/0138025 entitled Orthodontic Systems And Methods Including Parametric Attachments; U.S. Patent Application Publication No. 2011/0020761 by Kalili entitled Orthodontic Repositioning Appliance; U.S. Pat. No. 6,250,918 issued to Sachdeva et al. entitled Method And Apparatus For Simulating Tooth Movement For An Orthodontic Patient; and U.S. Patent Application Publication No. 2005/0074716 by Cleary et al. entitled Apparatus For Indirect Bonding Of Orthodontic Appliances And Method Of Making The Same.

However, each one of the previously mentioned references suffers from one or more of the following disadvantages. The referenced systems, methods and devices lack sufficient capacity to effectuate precise tooth movement in a clinically reliable and reproducible manner. The disclosed technology does not adequately resolve the problem of an increased need for mid-course corrections and refinements due to inaccurate attachment placement, and lengthy treatment times associated with imprecisely placed attachments. The disclosed technology also fails to address problems involving flash resulting from attachment placement, which may lead to patient discomfort during flash removal, imprecise aligner retention, and longer term periodontal disease.

For the foregoing reasons, a need exists for a method and apparatus to achieve accurate attachment fabrication and placement. In order for attachments to function effectively and produce desired patient outcomes, they must be applied to teeth with precision and minimal distortion due to variable such as practitioner technique, pressure variations applied to attachment templates, and overuse of composite applied to attachment templates resulting in undesirable excess, or flash. Flash is undesirable as its presence can hamper attachment fit and create patient discomfort during flash removal. In addition, flash can create rough edges around placed attachments, which can irritate patient gingival tissue and attract dental plaque, leading to oral hygiene problems and gingival tissue inflammation. Ultimately, flash can lead to gingival or gum tissue redness, swelling and inflammation, bleeding, pain, or halitosis. Composite flash can also form unsightly stains from certain foods, coffee, tea and smoking.

Application of the disclosed invention will result in the fabrication and placement of more precise attachments, and correspondingly more reliable purchase points for teeth to which tooth movement forces may be applied.

SUMMARY

The present invention is directed to a method and apparatus that will satisfy the existing need for fabricating and placing orthodontic attachments with precision and reliability. The disclosed invention will result in more accurate tooth movement and less excess bonding plastic (i.e., flash) on patent teeth after attachment placement, which will result in more desirable patient outcomes.

The invention comprises a method and apparatus for accurately applying orthodontic attachments (i.e. purchase and retention points) to human teeth in the process of using clear, plastic teeth aligners. The invention's primary application will be for use in the field of Orthodontic Biomechanics, which generally involves: (1) evaluating biologic considerations relating to tooth movement (at the cellular and molecular levels); and (2) engineering dental appliances capable of applying appropriate mechanical forces, typically to anchor certain teeth in place while applying movement forces to other teeth.

In order for attachments to function effectively, they must be applied to teeth with precision and minimal distortion due to variables such as practitioner technique, pressure variations applied to attachment templates, and overuse of composite applied to attachment templates, resulting in undesirable flash, which can hamper attachment fit and create patient discomfort during flash removal.

The inventive method delivers more precise attachments to teeth, and correspondingly more reliable purchase points for teeth, to which tooth movement forces may be applied. It is an object of the present invention to provide a method for applying attachments to human teeth comprising: constructing prefabricated attachments having a bioconcave base approximating the contours of the enamel surface of a patient's teeth; a retention register to facilitate transferring the prefabricated attachments from a model of a patient's teeth onto the enamel surface of a patient's teeth; and a distinct junction situated between the prefabricated attachments and retention register to facilitate removing the retention register from prefabricated attachments after the attachments are securely bonded onto a patent's teeth. The prefabricated attachments incorporate specific forms of force vector advantage to facilitate accurate positional placement of the prefabricated attachments onto a patient's teeth.

The bioconcave base of the prefabricated attachments is constructed to approximate various facial, buccal, lingual or palatal contours of the enamel surface of the teeth at the interface where the bioconcave base of the prefabricated attachments will be bonded to the enamel surface of the patient's teeth.

The retention register comprises multiple retention legs moldably attached to the retention register to form an undercut arch, and multiple slide-lock channels to secure prefabricated attachments into attachment delivery trays. The multiple retention legs of the retention register are color coded to create a distinct junction between prefabricated attachments and the retention register to facilitate accurate removal of the retention register and corresponding multiple retention legs after prefabricated attachments are placed onto a patient's teeth.

The undercut arch of the retention register is constructed with sufficient depth to create a snap-fit lock to prevent prefabricated attachments from falling out of prefabricated attachment delivery trays during handling, and sufficient weight to facilitate accurate separation of the retention register and corresponding prefabricated attachments from prefabricated attachment delivery trays after prefabricated attachments are placed onto a patient's teeth.

At least one channel is disposed adjacent to the retention legs of the retention register to facilitate single direction positioning of the retention register and corresponding prefabricated attachment into prefabricated attachment delivery trays. The retention register is fabricated into the facial surface of prefabricated attachments to facilitate fitting prefabricated attachments into corresponding delivery trays.

The distinct junction situated between the prefabricated attachments and the retention register comprises color coding the retention register's retention legs to facilitate accurately removing the retention register and corresponding retention legs after the prefabricated attachments are placed onto a patient's teeth. The distinct junction between the prefabricated attachments and the retention register may also comprise multiple demarcation scribe lines situated on the multiple retention legs of the retention register to facilitate accurate removal of the retention register and corresponding multiple retention legs after the prefabricated attachments are placed onto a patient's teeth.

The inventive method further comprises constructing attachment delivery trays having an inner shell to support the prefabricated attachments during delivery of the prefabricated attachments from a model of a patient's teeth onto the enamel surface of a patent's teeth, and an outer shell to facilitate handling the prefabricated attachments during delivery of the prefabricated attachments from a model of a patient's teeth onto the enamel surface of a patient's teeth. The inner shell of the attachment delivery tray is situated adjacent to the prefabricated attachments and comprises a flexible material to create a soft interface between the multiple retention legs of the retention register and the attachment delivery trays. The outer shell of the attachment delivery trays comprises a hard thermoplastic material to facilitate handling the attachment delivery trays before, during and after delivery of the prefabricated attachments onto a patient's teeth. The attachment delivery trays may also be constructed to accommodate a single prefabricated attachment for delivery to and placement onto a patient's tooth. Prefabricated attachments are subsequently placed into delivery trays to deliver the prefabricated attachments onto a patient's teeth.

The inventive method further comprises constructing an etching stencil having multiple openings to facilitate bonding adhesive application, and a molded dam to control etchant flow during application of etching material to the enamel surface of a patient's teeth. The etching stencil's molded dam is designed to diminish the presence of excess bonding plastic on a patient's teeth after prefabricated attachments are placed onto a patient's teeth. The multiple etching stencil opening are fabricated using laser technology to ensure that the multiple openings accurately approximate the intended location where acid etched enamel is desired for placement onto a patient's teeth.

The inventive method further comprises removing the etching stencil tray from the patient's teeth and rinsing and drying the patient's etched teeth; applying a bonding agent onto the patient's etched teeth intended to receive the prefabricated attachments; and applying a bonding adhesive onto the bioconcave base of the prefabricated attachments positioned in the attachment delivery tray.

The inventive method further comprises placing the attachment delivery tray containing prefabricated attachments onto the patient's teeth and setting the bonding materials with light curing; and subsequently removing the attachment delivery tray from the patient's teeth, leaving the bonded prefabricated attachments and corresponding retention register on the patient's teeth; and, finally, removing the retention register, leaving prefabricated attachments secured to the enamel surface of the patient's teeth.

The inventive method further comprises employing aligner company software to develop a patient treatment plan specifying desired types of prefabricated attachments and desired placement locations of the prefabricated attachments, and digital mapping to facilitate attachment placement in order to approximate the previously determined desired placement locations for the prefabricated attachments to be bonded onto a patient's teeth.

It is a further object of the present invention to provide a method for applying attachments to human teeth comprising: constructing a series of shapes of prefabricated attachments having a concave base; applying the prefabricated attachments onto a patient's teeth in advance of developing dental impressions or digital scans of the patient's teeth; developing dental impressions or scans of the patient's teeth and affixed prefabricated attachments; and forwarding the dental impressions or scans to an aligner manufacturer to determine the final shape and position of the prefabricated attachments on a patient's teeth and optimal force vector parameters corresponding to a prefabricated attachment delivery tray.

The prefabricated attachment shapes range in size from approximately 2 millimeters to 5 millimeters in width and length and 1 to 2 millimeters in depth, and incorporate variations comprising a quarter sphere, cuboid, triangular prisms, trapezium prisms or triangular based prisms, or other shapes that facilitate optimal force vectors and moments to be determined by the clinician. The concave base of the prefabricated attachments comprises concavity approximating the contours of the patient's teeth intended to receive the prefabricated attachments to facilitate smooth positioning of the prefabricated attachments onto a patient's teeth by a clinician.

The aligner manufacturer evaluates the patient's dental impressions or digital scans of the patient's teeth to determine whether previously applied prefabricated attachments accomplish desired tooth movement. The aligner manufacturer employs software reformulation to generate additional prefabricated attachments based on review of the patient's dental impressions or digital scans to modify placement location of previously positioned prefabricated attachments in order to accomplish desired tooth movement, and provide additional prefabricated attachments to the clinician in prefabricated attachment delivery trays.

It is a further object of the present invention to provide an apparatus for applying attachments to human teeth comprising: a retention register to facilitate transferring prefabricated attachments from a model of a patient's teeth onto the enamel surface of a patient's teeth; and an etching stencil used in conjunction with the retention register to diminish the presence of excess bonding plastic on a patient's teeth after prefabricated attachments are placed onto a patient's teeth. The retention register further comprises an undercut arch, and multiple retention legs moldably attached to the retention register to form at least one slide-lock channel to secure prefabricated attachments into attachment delivery trays.

The undercut arch of the retention register is constructed with sufficient depth to create a snap-fit lock to prevent prefabricated attachments from falling out of prefabricated attachment delivery trays during handling, and sufficient weight to facilitate accurate separation of the retention register and corresponding prefabricated attachments from prefabricated attachment delivery trays after prefabricated attachments are placed onto a patient's teeth. At lease one slide-lock channel is disposed adjacent to the plurality of retention legs of the retention register to facilitate single direction positioning of the retention register and corresponding prefabricated attachment into prefabricated attachment delivery trays.

The multiple retention legs of the retention register may be color coded to create a distinct junction between the prefabricated attachments and the retention register to facilitate accurate removal of the retention register and corresponding multiple retention legs after prefabricated attachments are placed onto a patient's teeth. In addition, multiple demarcation scribe lines may be positioned between the prefabricated attachments and the multiple retention legs of the retention register to create an additional distinct junction between the prefabricated attachments and the retention register to facilitate accurate removal of the retention register and corresponding multiple retention legs after prefabricated attachments are placed onto a patient's teeth. The retention register having multiple retention legs is fabricated into the facial surface of the prefabricated attachments to facilitate fitting the prefabricated attachments into corresponding delivery trays.

The etching stencil further comprises multiple openings to facilitate bonding adhesive application and a molded etchant limiting dam to control etchant flow during application of etching material to the enamel surface of a patient's teeth. The moldably disposed etchant limiting dam of the etching stencil is designed to diminish the flow of etchant to undesired areas enamel outside of the base of the attachment. The etching stencil's multiple openings are fabricated using laser technology to ensure that the multiple openings accurately approximate the intended location where acid etched enamel is desired for placement onto a patient's teeth. The etchant limiting dam is formed by compression of the thermoplastic tray material into a trough in the model of the patient's teeth. The trough outlines the base of the attachment.

The inventive method and apparatus provide several advantages that are desirable in the marketplace. The inventive prefabricated attachments are constructed to minimize the thickness of bonding adhesive that is used to bond prefabricated attachments to patient teeth, resulting in minimal flash. In addition, currently there is no good way to control the precise placement of etchant so that it etches only the desired boundaries of attachments. The inventive etching stencil addresses this problem by providing a tray, similar to aligners, that has precise laser cut openings where the intended acid etched enamel is desired. Employing the etching stencil ensures that adhesive bonds only to the desired enamel. Any minimal remaining flash is easily removable.

These and various other aspects, features, objects and advantages of the present invention will be described in more detail below in the detailed description of the invention and in conjunction with the following Figures.

DETAILED DESCRIPTION OF PREFERRED EMBODIMENTS

Figure 1:
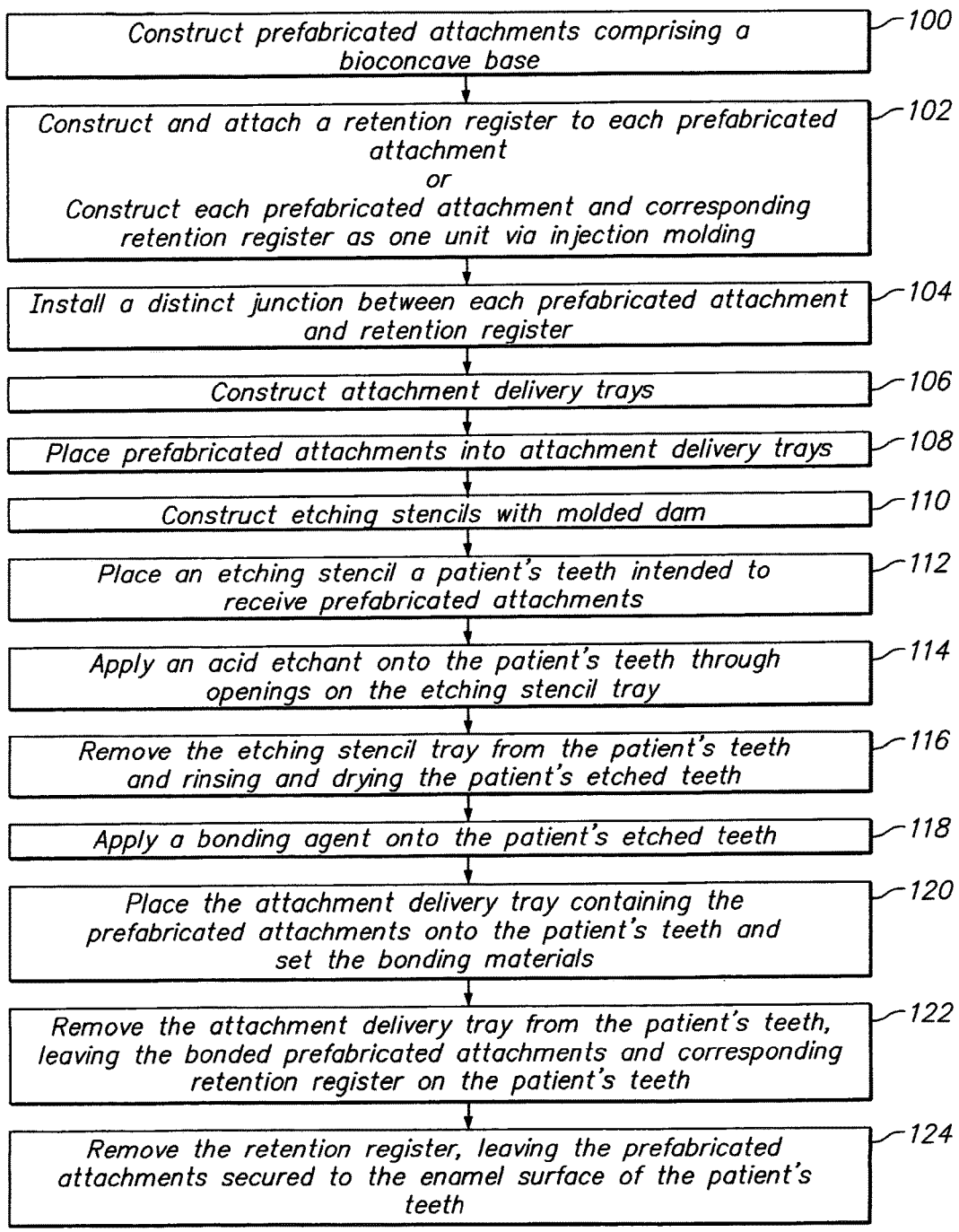
FIG. 1 is a block diagram describing some of the steps that are followed in applying attachments to patient teeth according to an embodiment of the present invention.

FIG. 1 is a block diagram describing some of the steps that are performed in delivering orthodontic attachments according to one embodiment of the present invention. Block 100 represents the step of constructing prefabricated attachments, with each prefabricated attachment having a bioconcave base. Attachments are prefabricated by aligner manufacturers, or attachment prefabrication is subcontracted out to suitable industry participants. Prefabricated attachments are constructed of a composite plastic or resin material according to aligner manufacturer specifications, most likely employing a composite resin that is lightly filled with small particle silica filler. Prefabricated attachment shapes and contours are constructed according to aligner company specifications regarding optimal force applications, aligner retention, and tooth tracking aligner trays over the course of a patient's treatment plan. The inventive attachments are fabricated to incorporate specific forms of force vector advantage to facilitate accurate positional placement onto a patient's teeth. Prefabricated attachments can be formed by injection molding of light, sensitive composite material and set with light curing. The prefabricated attachments will have a biconcave base approximating the various facial/buccal, or in some cases lingual/palatal, contours of the enamel surface of the teeth at the interface where the base of the prefabricated attachments will be bonded to the enamel surface of a patient's teeth. The purpose of this design is to minimize the thickness of bonding adhesive that will be used to bond the prefabricated attachment in order to minimize excess bonding adhesive (i.e., "flash").

In another embodiment of the present invention, aligner manufacturer software is employed to develop a patient treatment plan, specifying desired types of prefabricated attachments and desired placement locations for those prefabricated attachments. In addition, digital mapping is employed to facilitate placement of the prefabricated attachments to approximate previously determined desired placement locations for prefabricated attachments to be bonded onto a patient's teeth.

In block 102, the prefabricated attachments described in block 100 are adapted to incorporate a positive seat, sure fit, snap fit retention register, which is fabricated into the facial surface of prefabricated attachments to create a one-way fit for attachments into corresponding attachment delivery trays. Each retention register is constructed with at least one slide-lock channel and multiple retention legs to facilitate fitting attachments into corresponding prefabricated attachment delivery trays. Retention legs are attached at a distinct junction between prefabricated attachments and corresponding retention registers to facilitate accurate retention of prefabricated attachments in attachment delivery trays and accurate transfer of prefabricated attachments from attachment delivery trays onto a patient's teeth. The multiple retention legs of each retention register are disposed to create at least one slide lock channel to facilitate securing prefabricated attachments in corresponding attachment delivery trays. Retention legs also provide for accurate detachment of attachment delivery trays from prefabricated attachments and corresponding retention registers after prefabricated attachments are placed onto a patient's teeth.

Each retention register also comprises an undercut arch to facilitate securing prefabricated attachments into corresponding delivery trays, and is constructed deep enough to prevent prefabricated attachments from falling out of, or otherwise disengaging from, corresponding attachment delivery trays during packaging and handling. Each undercut arch is geometrically shaped so that prefabricated attachments and retention legs will easily separate from attachment delivery trays with light force when desired. Optionally, the prefabricated attachments described in block 100 and corresponding retention registers may be constructed as one unit using injection molding. Retention registers facilitate transferring prefabricated attachments from a model of a patient's teeth onto the enamel surface of a patient's teeth.

As represented by block 104, a distinct junction is fabricated between the prefabricated attachments described in block 100 and the retention registers described in block 102. The distinct junction is fabricated to incorporate multiple demarcation scribe lines, disposed on the multiple retention legs of the retention registers described in block 102, to facilitate accurate removal of retention registers and corresponding multiple retention legs after the prefabricated attachments described in block 100 are placed onto a patient's teeth. The distinct junction may also be fabricated to incorporate color coding retention register retention legs to facilitate accurate removal of retention registers and corresponding retention legs after prefabricated attachments are placed onto a patient's teeth.

In block 106, attachment delivery trays are constructed having an inner soft, resilient shell to support prefabricated attachments during delivery of prefabricated attachments from a model of a patient's teeth onto the enamel surface of a patient's teeth, and a harder outer shell to facilitate handling prefabricated attachments during delivery of prefabricated attachments from a patient model onto a patient's teeth. The attachment delivery tray inner shell is positioned adjacent to prefabricated attachments and constructed to incorporate a flexible material, which creates a soft interface between retention legs of retention registers and attachment delivery trays. The attachment delivery tray outer shell is constructed using a hard, ridged theromoplastic material to facilitate handling attachment delivery trays before, during and after prefabricated attachments are delivered onto a patient's teeth. Attachment delivery trays are constructed to accommodate either a single prefabricated attachment, or multiple prefabricated attachments, for delivery to and placement onto a patient's teeth.

As shown in block 108, prefabricated attachments are placed into corresponding attachment delivery trays. Individual prefabricated attachments can be placed into the delivery trays in various ways. For instance, prefabricated attachments can be placed into corresponding attachment delivery trays manually by technicians at the site where aligners and delivery trays are fabricated and packaged. A coding system can be used to indicate to a technician which particular shape goes into a corresponding slot in the delivery trays. Variable retention register shapes may be employed to facilitate prefabricated attachment placement and the shapes of the retention registers can be adapted to aid in placement. Alternatively, robotic or otherwise automated machinery may be used to place prefabricated attachments into corresponding attachment delivery trays.

As represented in block 110, etching stencils with corresponding molded dam components are constructed to facilitate accurate bonding plastic application to a patient's teeth and thereby diminish, or completely eliminate, the accumulation of flash on a patient's teeth resulting from prefabricated attachment placement. The etching stencil is fabricated in the form of a tray, which is similar in shape to conventional teeth aligners. The molded dam on each etching stencil is constructed to limit etchant flow and diminish the presence of excess bonding plastic on a patient's teeth after prefabricated attachments are placed onto a patient's teeth. Each etching stencil is also constructed to incorporate multiple openings to facilitate accurate etchant application to a patient's teeth. Each molded dam is constructed as a slightly raised outline of etching stencil tray material, disposed around the multiple openings of the etching stencil on the tooth side of the etching stencil to facilitate tight adherence of the etching stencil to teeth during etching, and prevent undesired acid etchant creeping during flushing of a patient's acid etched teeth. Each molded dam is fabricated by laser cutting a small trough around a model of the patient's teeth on the borders of the desired prefabricated attachment location, so that the molded dam is created in the thermoplastic creation of the etching stencil. Each laser cut trough is approximately 0.1 to 0.25 mm in depth and width. An alternate method of trough fabrication is to incorporate trough design into three-dimensional molding by aligner manufacturers and produce three-dimensional printed resin models with the troughs corresponding to the base of the corresponding attachment.

Block 112 shows that the etching stencil described in block 110 is placed onto patient teeth intended to receive the prefabricated attachments described in block 100. According to box 114, an acid etchant is placed onto a patient's teeth through the multiple openings fabricated on the etching stencil in exact locations where acid etched tooth enamel is desired. The acid etching material is limited under the etching stencil by the molded dam that outlines the multiple openings described above in block 110. According to box 116, the etching stencil is then removed for a second light flushing of the teeth with a fluid, such as water, and the patient's etched teeth are then dried. According to box 118, a commercially available bonding agent is applied to the patient's etched teeth in the area where the prefabricated attachments are to be placed, and a commercially available flowable bond adhesive is placed on the bioconcave base of the prefabricated attachments secured in corresponding attachment delivery trays.

In block 120, attachment delivery trays containing prefabricated attachments are placed onto a patient's teeth, and the bonding materials are set with a curing light. According to box 122, the attachment delivery tray is removed from the patient's teeth after bonding materials curing, leaving bonded prefabricated attachments in place on the patient's teeth along with the corresponding retention register and protruding multiple retention legs. According to box 124, the clinician removes the retention register from the patient's teeth. The clinician first checks to ensure that prefabricated attachments are securely bonded to the patient's teeth, and subsequently removes the corresponding retention register by erasing the protruding multiple retention legs with a rotary dental handheld device, leaving accurate and consistent prefabricated attachments with minimal or no flash.

Figure 2:
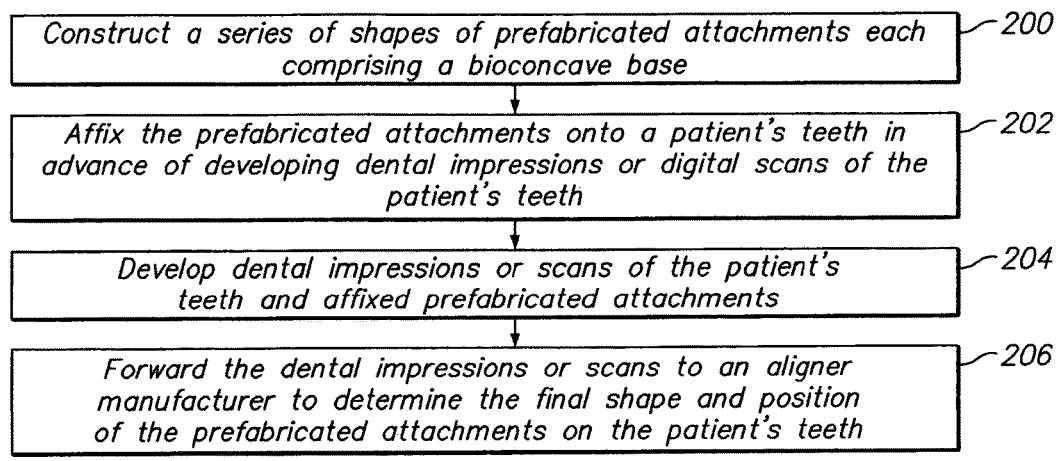
FIG. 2 is a block diagram describing some of the steps that are followed in applying attachments to patient teeth according to an embodiment of the present invention.
Figure 3:
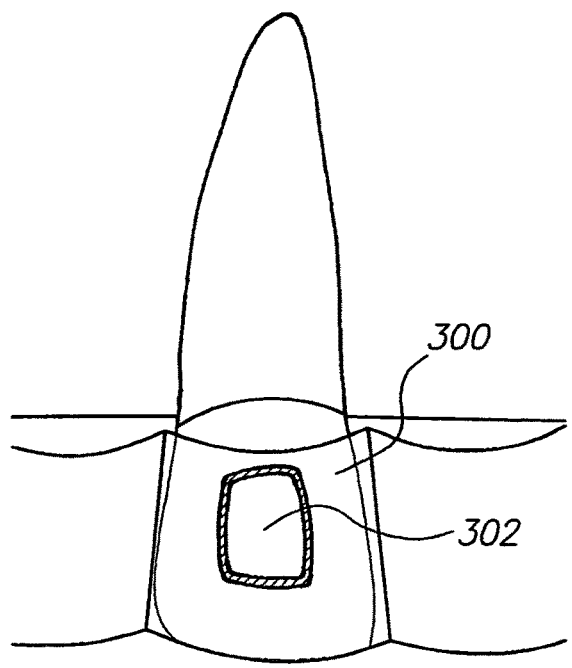
FIG. 3 is a perspective view of the inventive etching stencil placed on a patient tooth according to an embodiment of the present invention.

FIG. 2 is a block diagram describing some of the steps that are performed in delivering orthodontic attachments according to another embodiment of the present invention. Block 200 represents the step of constructing a series of prefabricated attachments having various shapes and each prefabricated attachment including a bioconcave base. Prefabricated attachment shapes range in size from 2 mm to 5 mm in width and length, and 1 mm to 2 mm in depth. In addition, prefabricated attachment shapes incorporate variations, such as a quarter sphere, cuboid, triangular prisms, trapezium prisms or triangular based prisms. The bioconcave base of each prefabricated attachment is made with concavity approximating the contours of a patient's teeth intended to receive prefabricated attachments. The concavity dimension of each bioconcave base facilitates smooth positioning of each prefabricated attachment onto a patient's teeth by a clinician.

In block 202, a clinician affixes prefabricated attachments onto a patient's teeth before developing dental impressions or digital scans of the patient's teeth. According to box 204, the clinician then develops dental impressions or digital scans of the patient's teeth and affixed prefabricated attachments. According to box 206, the clinician then forwards the patient's dental impressions and/or digital scans to an aligner manufacturer to determine the final shape and position of prefabricated attachments to be delivered to the patient's teeth. In making this determination, the aligner manufacturer evaluates the dental impressions and/or digital scans of the patient's teeth to determine whether previously applied prefabricated attachments accomplish desired tooth movement. The aligner manufacturer may employ software reformulation to generate additional prefabricated attachments, based on review of the patient's dental impressions and/or digital scans, to modify placement location of previously positioned prefabricated attachments in order to accomplish desired tooth movement and provide additional prefabricated attachments to the clinician in corresponding attachment delivery trays.

Upon receipt of the additional prefabricated attachments from the aligner manufacturer, the clinician uses corresponding mapping provided by the aligner manufacturer in placing the additional prefabricated attachments to approximate ideal strategic locations of the additional prefabricated attachments for optimal biomechanical advantage. In addition, the clinician carefully etches only the precise area where the additional prefabricated attachments are to be placed and uses a small amount of bonding adhesive and flowable adhesive, which will minimize or completely eliminate the accumulation of excess material or flash.

An orthodontic prefabricated attachment application appliance, comprising an etching stencil (300) and retention register (400), is used to apply prefabricated attachments (500) to human teeth (600). FIGS. 3-6 show etching stencil (300), which has at least one stencil opening (302) and a dam (304) constructed to outline stencil opening (302) to control etchant flow during application of etching material to the enamel surface of a patient's teeth (600).

FIGS. 7-21 show retention register (400) in conjunction with prefabricated attachment (500), including various shapes of attachments (500(*a*)-500(*g*).) Prefabricated attachments (500) and attachments (500(*a*)-500(*b*) each have a bioconcave base (502), which approximates the contours of the enamel surface of a patient's teeth (600). Retention register (400) has multiple retention legs (402) that are attached to retention register (400) via injection molding or other suitable fabrication technique, such as wax patterns to create solid metal dies with lost wax or computer software generated using three-dimensional modeling and three-dimensional STL printing. Retention legs (402) form a least one slide-lock channel (404) to secure prefabricated attachments (500) into an attachment delivery tray (700). Retention legs (402) may be color coded to create a visibly distinct junction between each prefabricated attachment (500) and corresponding retention register (400) to facilitate accurate removal of retention register (400) and retention legs (402) after each prefabricated attachment (500) is placed onto the surface of a patient's teeth (600). In addition, or as an alternative, to color coded retention legs (402), multiple demarcation scribe lines may be positioned between each prefabricated attachment (500) and retention legs (402) of each retention register (400) to create a visibly distinct junction between each prefabricated attachment (500) and corresponding retention register (400) to facilitate accurate removal of retention register (400) and corresponding retention legs (402) after prefabricated attachment (500) placement onto the surface patient's teeth (600). Retention register (400) having multiple retention legs (402) may be fabricated, via injection molding or other suitable fabrication technique, such as three-dimensional computer modeling, into the facial surface of prefabricated attachments (500) to facilitate fitting prefabricated attachments (500) into corresponding delivery trays (700).

FIG. 15, FIGS. 17-21 and FIGS. 22-23 show attachment delivery tray (700), which has inner shell (702) and outer shell (704) Inner shell (702) of attachment delivery tray (700) is made from a flexible material, such as household hot melt glue gun material or thermoplastic mouth guard material, to create a soft interface between retention legs (402) of each retention register (400) and each attachment delivery tray (700). Outer shell (704) of each attachment delivery tray (700) is made of a hard polypropylene or polyester thermoplastic material, such as Essix A or Great Lake A, before, during and after one or more attachments (500(a)-500(g)) are delivered to a patient's teeth (600). Attachment delivery trays (700) are not made for the clinical fabrication of attachments (500(a)-500(g)), but rather for delivery of one or more prefabricated attachments (500(a)-500(g)) with corresponding retention registers (400). Attachment delivery trays (700) may be provided in whole dental arch trays, sectional trays with three or six prefabricated attachments (500(a)-500(g)) per attachment delivery tray (700), or in an attachment delivery tray (700) for a single prefabricated attachment (500(a)-500(g)) (also known as "jigs").

In practice, attachment delivery trays (700) with an assortment of inserted prefabricated attachments (500(a)-(g)) arrive at a dental office packaged in clearly demarcated packages. At the appointed time chosen for delivery of one or more assorted prefabricated attachments (500(a)-500(g)) onto a patient's teeth (600), the clinician should inspect each attachment delivery tray (700) to ensure that prefabricated attachments (500(a)-500(g)) are seated correctly in corresponding attachment delivery trays (700). The clinician should also check to ensure that a pre-attachment aligner fits properly onto the patient's teeth before proceeding with delivery of one or more prefabricated attachments (500(a)-500(g)). The clinician then cleans the patient's teeth (600) with non-fluoridated pumice, or a similar compound, using rotary instruments and rinses the teeth (600) to receive one or more prefabricated attachments (500(a)-500(g)). Conventional cheek retractors are used as necessary.

Figure 4:
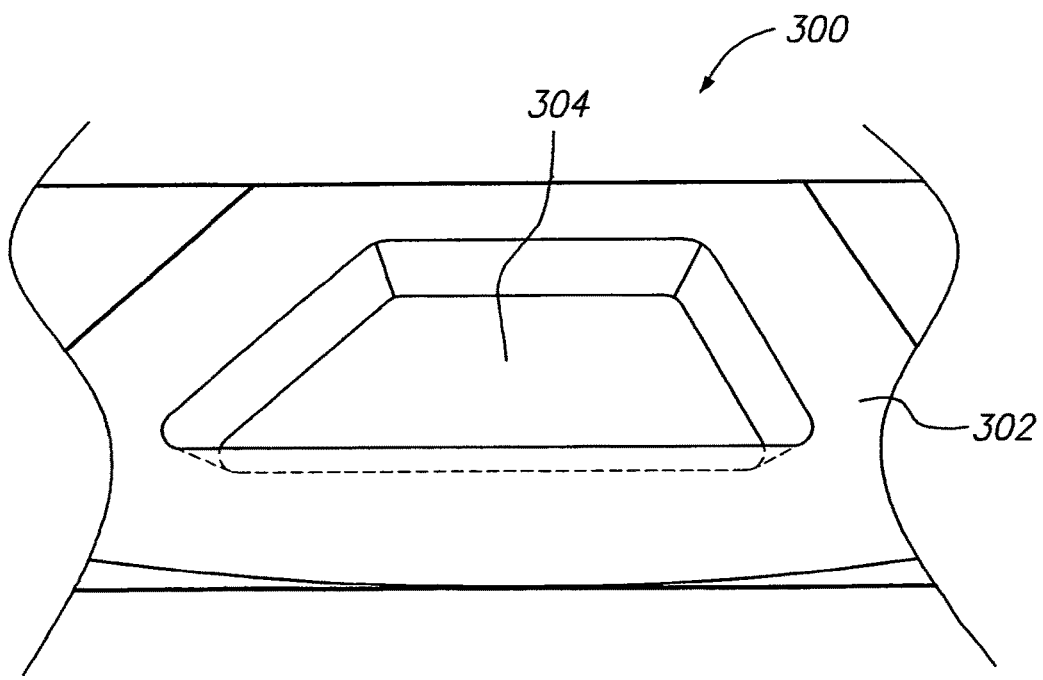
FIG. 4 is an exploded view of the inventive etching stencil and etchant limiting dam according to an embodiment of the present invention.
Figure 5:
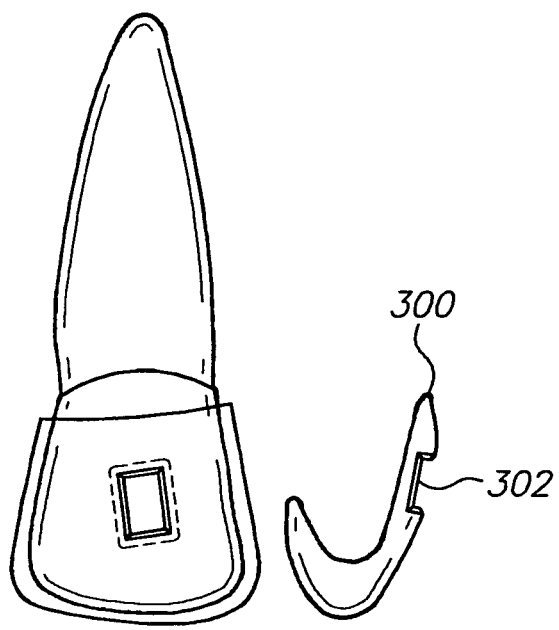
FIG. 5 is a perspective view of the inventive etching stencil placed on a patient tooth and a side view of the inventive etching stencil off of a patient tooth according to an embodiment of the present invention.
Figure 6:
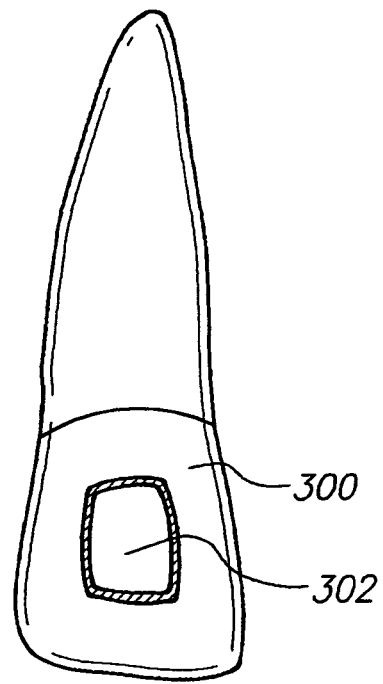
FIG. 6 is a perspective view of the inventive etching stencil on a patient tooth according to an embodiment of the present invention.
Figure 7:
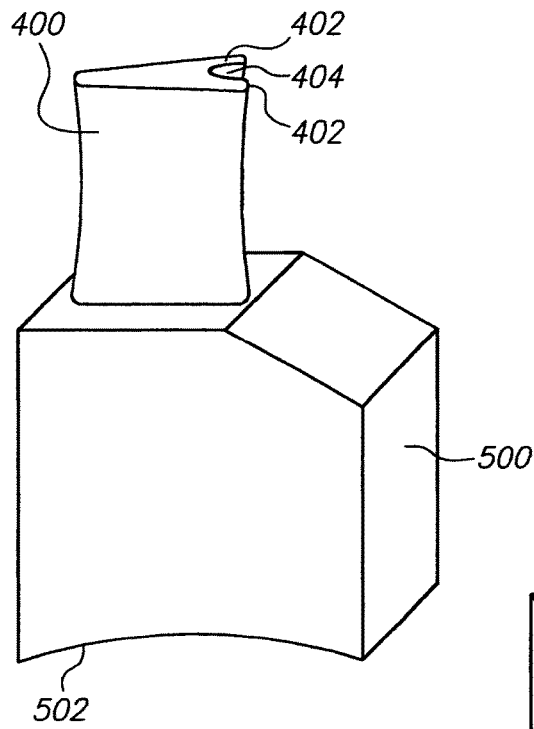
FIG. 7 is a side view of an alternate shape of an inventive attachment and retention register according to an embodiment of the present invention.
Figure 8:
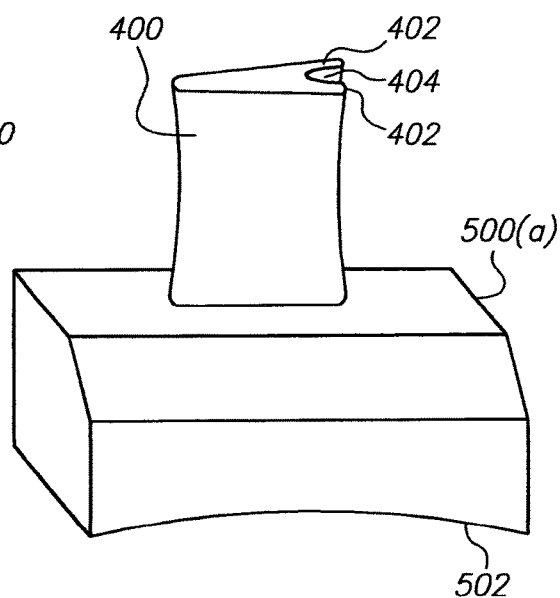
FIG. 8 is a side view of an alternate shape of an inventive attachment and retention register according to an embodiment of the present invention.
Figure 9:
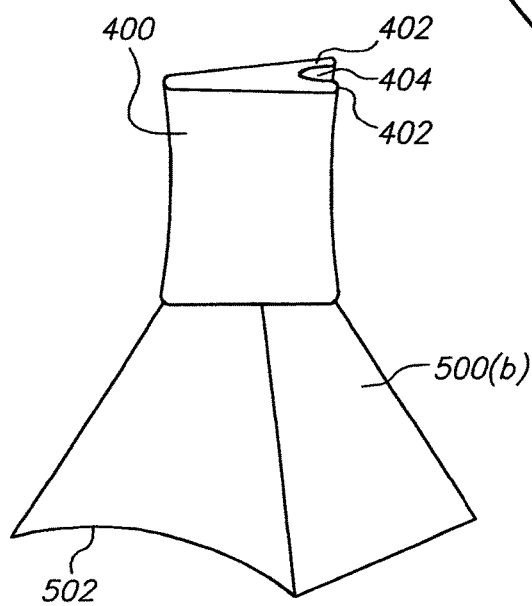
FIG. 9 is a side view of an alternate shape of an inventive attachment and retention register according to an embodiment of the present invention.
Figure 11:
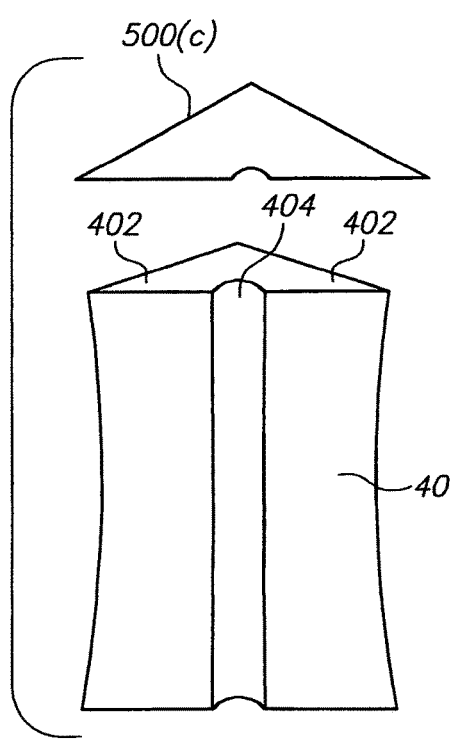
FIG. 11 is an exploded view of an alternate shape of an inventive attachment and retention register according to an embodiment of the present invention.
Figure 10:
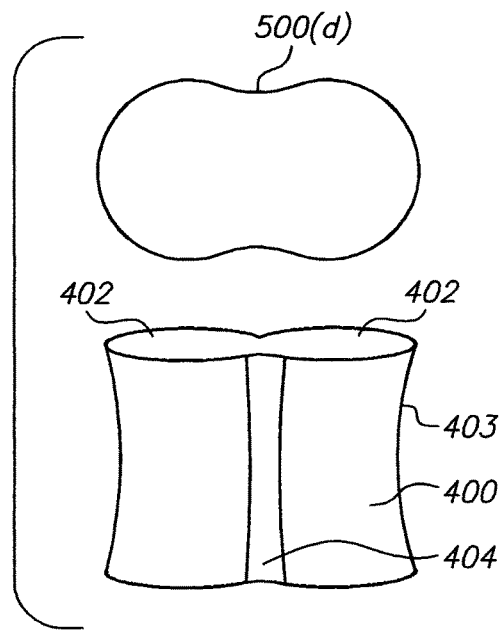
FIG. 10 is an exploded view of an alternate shape of an inventive attachment and retention register according to an embodiment of the present invention.
Figure 12:
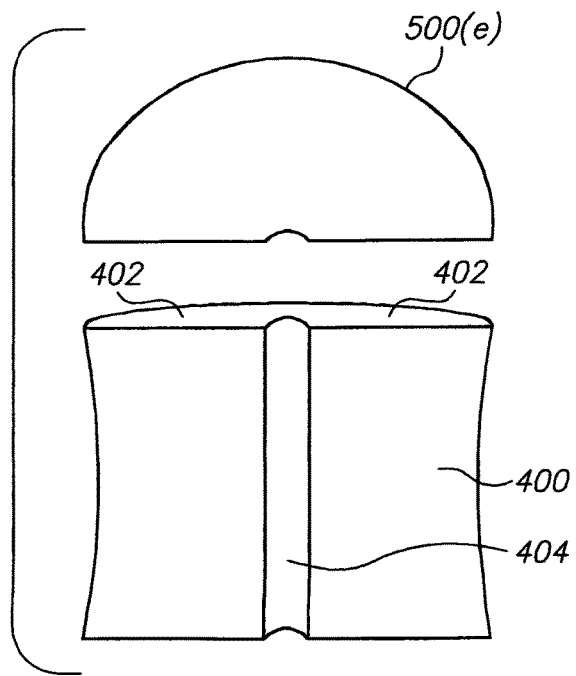
FIG. 12 is an exploded view of an alternate shape of an inventive attachment and retention register according to an embodiment of the present invention.
Figure 13:
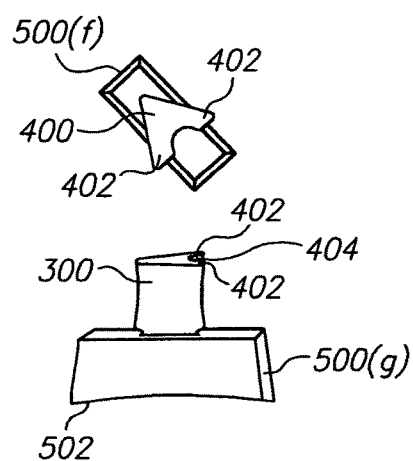
FIG. 13 is a top view and side view of an alternate shape of an inventive attachment and retention register according to an embodiment of the present invention.
Figure 14:
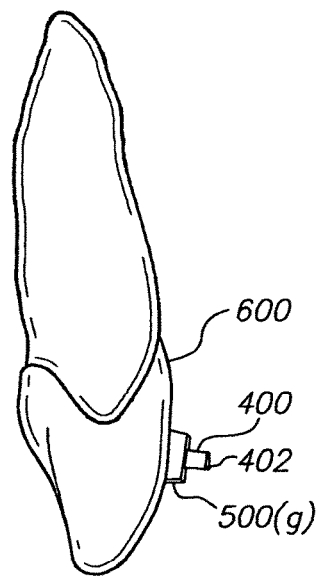
FIG. 14 is a side view of a patient tooth with an alternate shape of an inventive attachment and retention register prior to removal of the retention register according to an embodiment of the present invention.
Figure 15:
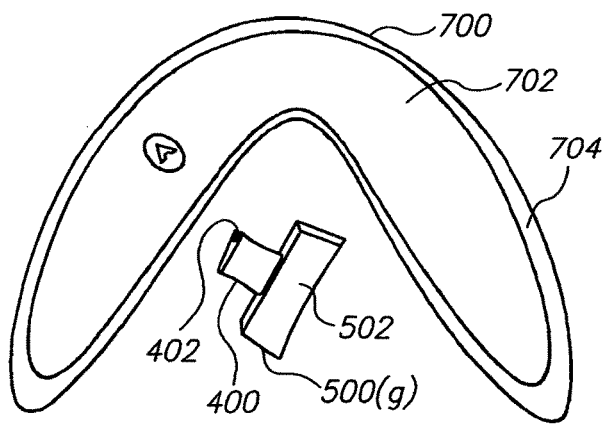
FIG. 15 is a side perspective view of an alternate shape of an inventive attachment and retention register, and an inventive attachment delivery tray (with an exemplary attachment and retention register inserted) according to an embodiment of the present invention.
Figure 16:
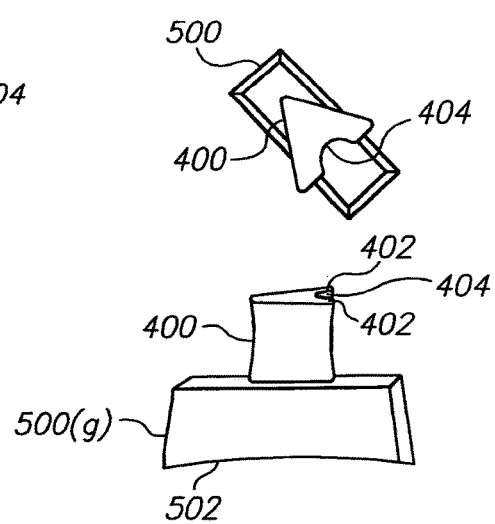
FIG. 16 is a top view and side view of an alternate shape of an inventive attachment and retention register according to an embodiment of the present invention.
Figure 17:
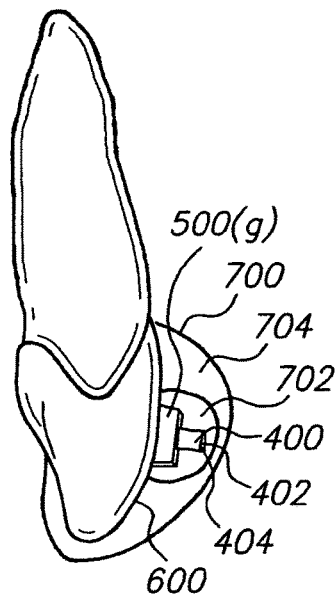
FIG. 17 is a side view of a patient tooth with an alternate shape of an inventive attachment, retention register and attachment delivery tray with inner shell and outer shell attached prior to removal of the delivery tray and retention register according to an embodiment of the present invention.
Figure 18:
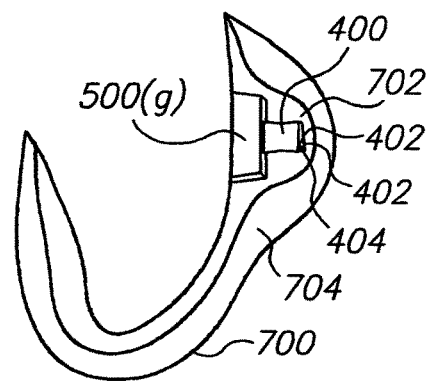
FIG. 18 is a side view of an alternate shape of an inventive attachment, retention register and attachment delivery tray with inner shell and outer shell according to an embodiment of the present invention.
Figure 19:
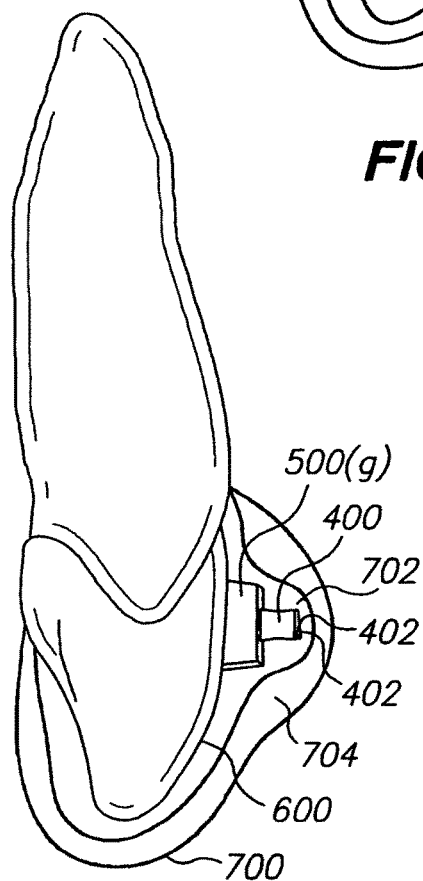
FIG. 19 is a side view of a patient tooth with an alternate shape of an inventive attachment, retention register and delivery tray with inner shell and outer shell attached prior to removal of the delivery tray and retention register according to an embodiment of the present invention.
Figure 20:
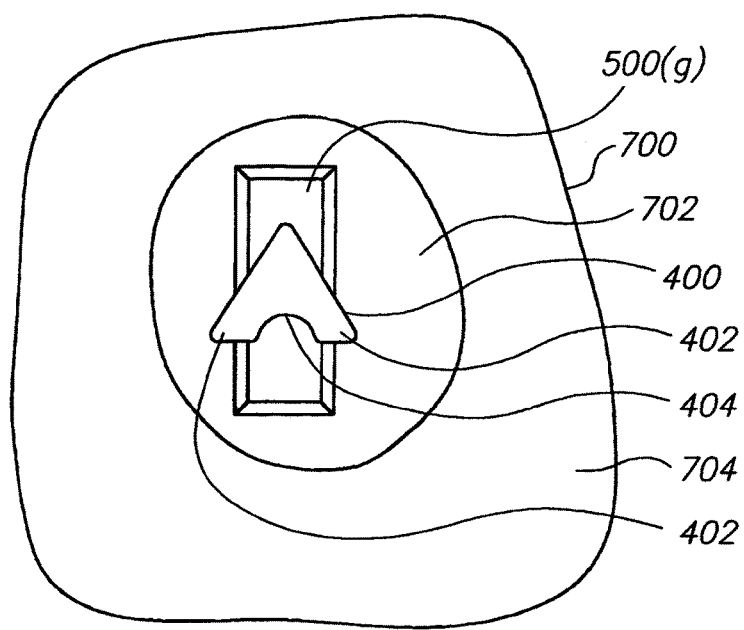
FIG. 20 is a top perspective view of an alternate shape of an inventive attachment, retention register and attachment delivery tray on a patient tooth prior to removal of the attachment delivery tray and retention register according to an embodiment of the present invention.
Figure 21:
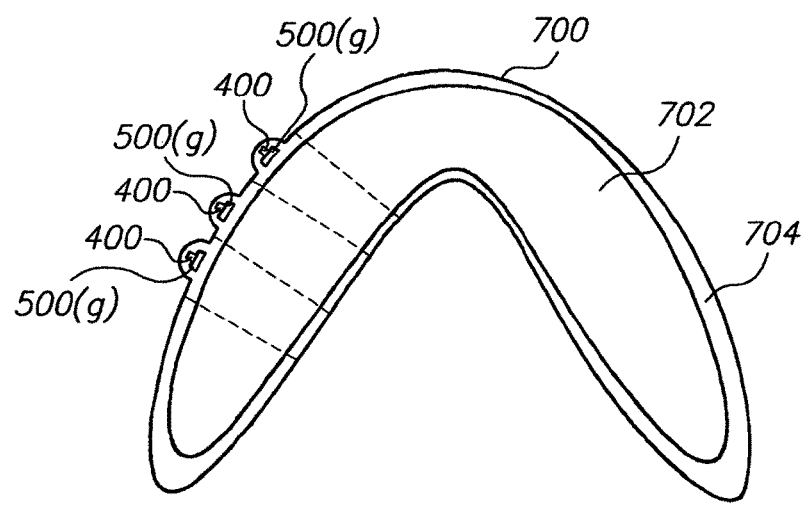
FIG. 21 is a side perspective view of multiple inventive attachments and retention registers positioned in an attachment delivery tray according to an embodiment of the present invention.

FIGS. 3-6 show etching stencil (300). Patient teeth (600) are etched in the area to receive at least one prefabricated attachment (500(a)-500(g)) using etching stencil (300). The clinician will use an etchant such as mild phosphoric acid before rinsing and drying patient teeth (600). The acid etchant material is limited under etchant stencil (300) by etching stencil dam (304) that outlines the etching stencil opening (302). As shown in FIG. 4, etching stencil dam (304) is a slightly raised outline of tray material around etching stencil opening (302) on the tooth side of etching stencil (300) to assure tight adherence of etching stencil (300) to patient teeth (600) during etching, and prevent undesired creeping of etchant material during flushing. Etching stencil dam (304) is fabricated by laser cutting a small trough around a model of patient teeth on the border of each desired location for at least one prefabricated attachment (500(a)-500(g)), so that etching stencil dam (304) is created in the thermoplastic creation of etching stencil (300). Etching stencil dam (304) should be approximately 0.1 mm to 0.25 mm in depth and width.

A conventional bonding agent is then applied to each tooth in the area where one or more prefabricated attachment (500(a)-500(g)) is to be placed. The clinician then places a relatively small amount of a conventional flowable bond adhesive onto bioconcave base (502) of each prefabricated attachment (500(a)-500(g)) positioned in attachment delivery tray (700).

Figure 22:
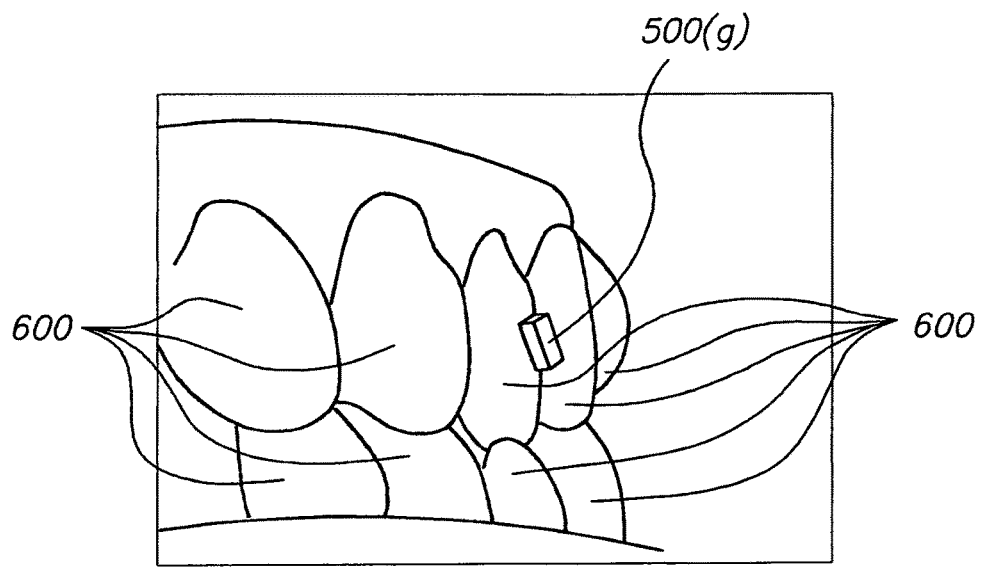
FIG. 22 is a side perspective view of an alternate shape of an inventive attachment attached to a patient tooth after removal of the retention register and attachment delivery tray according to an embodiment of the present invention.
Figure 23:
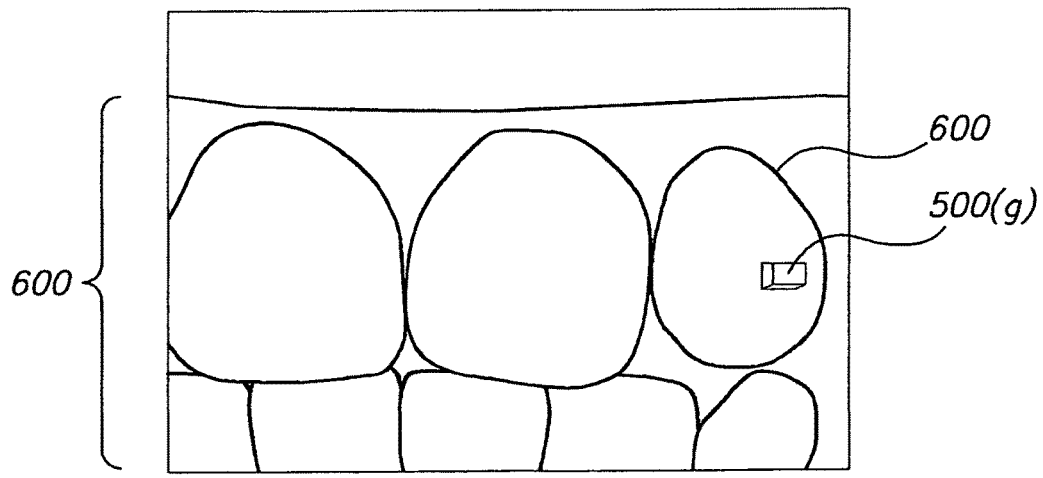
FIG. 23 is a front perspective view of an alternate shape of an inventive attachment attached to a patient tooth after removal of the retention register and attachment delivery tray according to an embodiment of the present invention.
Figure 24:
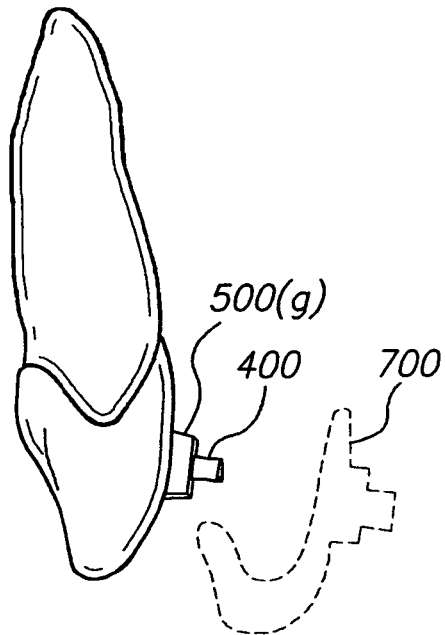
FIG. 24 is a side view of a patient tooth with an alternate shape of an inventive attachment and retention register attached after removal of the delivery tray (shown in broken lines for illustrative purposes) according to an embodiment of the present invention.
Figure 25:
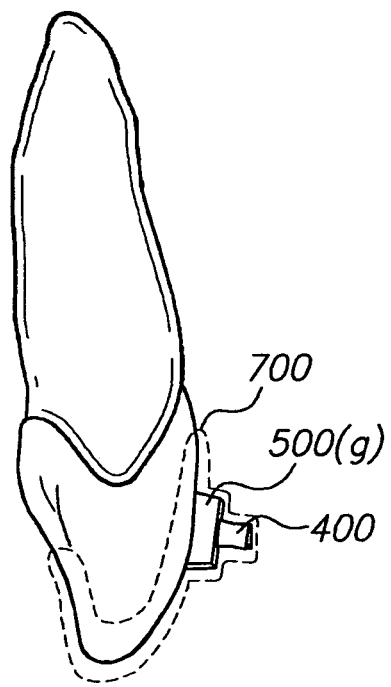
FIG. 25 is a side view of a patient tooth with an alternate shape of an inventive attachment, retention register and delivery tray (shown in broken lines for illustrative purposes) attached prior to removal of the delivery tray and retention register according to an embodiment of the present invention.

As shown in FIG. 22, attachment delivery tray (700) is then placed onto patient teeth (600) and a conventional bonding material is set with a curing light. As shown in FIG. 23, after curing is complete, attachment delivery tray (700) is then removed from patient teeth (600), leaving at least one bonded prefabricated attachment (500(a)-500(g)) with retention register legs (402) protruding. The clinician then checks each bonded prefabricated attachment (500(a)-500(g)) to ensure accurate bonding, and then removes retention legs (402) and any excess flash with a sharp dental instrument such as a scaler or gold foil knife, leaving at least one accurate prefabricated attachment (500(a)-500(g)) in place on patient teeth (600).

In an alternate embodiment of the present invention, an initial image of patient teeth (600) and bite registration are sent to an existing aligner company. Patient teeth imaging and bite registration may be performed using a conventional intraoral digital scanner on either full resolution scan (i.e., 15 minutes) or a shorter scan (i.e., 5 minutes). For offices without a digital scanner either polyvinyl siloxane (PVS) impressions, 100 hour alginate impressions, or standard plaster study models may be substituted, but it is noted that these may not be optimal substitutes for digital intraoral scans. The clinician and the aligner company technician together develop an aligner treatment plan with specification of at least one strategic attachment type (500(a)-500(g)) and locations with the aid of aligner manufacturer software. The clinician uses the mapping provided by the aligner technician in the placement of at least one specific prefabricated attachment (500(a)-500(g)) to approximate closely the ideal strategic location of at least one prefabricated attachments (500(a)-500(g)) for optimal biomechanical advantage.

The clinician utilizes care in etching only the precise area where at least one prefabricated attachment (500(a)-500(g)) is to be placed, and uses a relatively small amount of a conventional bonding liquid and a relatively small amount of a conventional flowable adhesive. Such care is taken to minimize the occurrence of excess material or flash. Notably, with this method no flash removal or no sculpting or shaping of prefabricated attachment(s) (500(a)-500(g)) is necessary.

Training trays are constructed in the dental office by the clinical team so that the patient can get used to aligners while the aligners are being made, and the patient's concern of having prefabricated attachment(s) (500(a)-500(g)) with no trays is addressed. A high resolution scan or PVS impression of patient teeth (600) is taken and sent to the aligner company for construction of the aligners.

The foregoing is considered illustrative only of the principles of the present invention. Various other objects, advantages and features of the present invention will become readily apparent to those of ordinary skill in the art, and the novel features will be partially pointed out in the appended claims. While the invention has been described with reference to at least one preferred embodiment, it is to be clearly understood by those skilled in the art that the invention is not limited thereto. Rather, the scope of the present invention is to be interpreted in conjunction with the appended claims.

I claim:

1. A method for applying attachments to human teeth comprising the steps of:
   (A) constructing prefabricated attachments having a bioconcave base approximating the contours of the enamel surfaces of a patient's teeth, a retention register to facilitate transferring said prefabricated attachments from a model of a patient's teeth onto the enamel surfaces of a patient's teeth, and a distinct junction between said prefabricated attachments and said retention register to facilitate removing said retention register from said prefabricated attachments;
(B) constructing attachment delivery trays having an inner shell to support said prefabricated attachments during delivery of said prefabricated attachments from a model of a patient's teeth onto the enamel surfaces of a patent's teeth, and an outer shell to facilitate handling said prefabricated attachments during delivery of said prefabricated attachments from a model of a patient's teeth onto the enamel surfaces of a patient's teeth;
(C) placing said prefabricated attachments into said delivery trays;
(D) constructing an etching stencil having a plurality of openings to facilitate bonding adhesive application and a moldably disposed dam to control etchant flow during application of etching material to the enamel surfaces of a patient's teeth;
(E) placing said etching stencil securely onto a patient's teeth intended to receive said prefabricated attachments;
(F) applying an acid etchant onto the patient's teeth through said plurality of openings disposed on an etching stencil tray;
(G) removing said etching stencil tray from the patient's teeth and rinsing and drying the patient's etched teeth;
(H) applying a bonding agent onto the patient's etched teeth intended to receive said prefabricated attachments;
(I) applying a bonding adhesive onto said bioconcave base of said prefabricated attachments positioned in said attachment delivery trays;
(J) placing said attachment delivery trays containing said prefabricated attachments onto the patient's teeth and setting bonding materials with light curing;
(K) removing said attachment delivery trays from the patient's teeth, leaving said bonded prefabricated attachments and corresponding retention registers on the patient's teeth; and
(L) removing said retention registers, leaving said prefabricated attachments secured to the enamel surfaces of the patient's teeth.

2. A method for applying attachments to human teeth according to claim 1 wherein said attachments comprise specific forms of force vector and movement advantage to facilitate accurate positional placement of said prefabricated attachments onto a patient's teeth.

3. A method for applying attachments to human teeth according to claim 1 wherein said retention register comprises a plurality of retention legs attached at said distinct junction to facilitate accurate retention of said prefabricated attachments in said attachment delivery trays and accurate transfer of said prefabricated attachments from said attachment delivery trays onto the patient's teeth.

4. A method for applying attachments to human teeth according to claim 3 wherein said distinct junction between said prefabricated attachments and said retention register comprises color coding said retention legs of said retention register to facilitate accurate removal of said retention register and corresponding retention legs after said prefabricated attachments are placed onto a patient's teeth.

5. A method for applying attachments to human teeth according to claim 3 wherein said distinct junction between said prefabricated attachments and said retention register comprises a plurality of demarcation scribe lines disposed on said plurality of retention legs of said retention register to facilitate accurate removal of said retention register and corresponding said plurality of retention legs after said prefabricated attachments are placed onto a patient's teeth.

6. A method for applying attachments to human teeth according to claim 1 wherein an inner shell of said attachment delivery tray is disposed adjacent to said prefabricated attachments and comprises a flexible material to create a soft interface between said retention legs of said retention register and said attachment delivery trays.

7. A method for applying attachments to human teeth according to claim 1 wherein said outer shell of said attachment delivery trays comprises a hard thermoplastic material to facilitate handling said attachment delivery tray's before, during and after delivery of said prefabricated attachments onto a patient's teeth.

8. A method for applying attachments to human teeth according to claim 1 wherein said moldably disposed dam of said etching stencil limits etchant flow and diminishes the presence of excess bonding plastic on a patient's teeth after said prefabricated attachments are placed onto a patient's teeth.

9. A method for applying attachments to human teeth according to claim 1 wherein said attachment delivery trays are constructed to accommodate a single prefabricated attachment for delivery to and placement onto a patient's tooth.

10. A method of applying attachments to human teeth according to claim 1 wherein said bioconcave base of said prefabricated attachments is constructed to approximate various facial, buccal, lingual or palatal contours of the enamel surfaces of the teeth at the interface where said bioconcave base of said prefabricated attachments will be bonded to the enamel surfaces of the patient's teeth.

11. A method of applying attachments to human teeth according to claim 1 wherein said retention register having a plurality of retention legs is fabricated into the facial surface of said prefabricated attachments to facilitate fitting said prefabricated attachments into said attachment delivery trays.

12. A method of applying attachments to human teeth according to claim 11 wherein said retention legs of said retention register are disposed to create an undercut arch and channel to secure said prefabricated attachments into said attachment delivery trays.

13. A method of applying attachments to human teeth according to claim 12 wherein said undercut arch is fabricated to prevent said prefabricated attachments from disengaging said attachment delivery trays during handling and packaging of said prefabricated attachments, and providing for accurate detachment of said attachment delivery trays from said prefabricated attachments and said retention registers after said prefabricated attachments are placed onto a patient's teeth.

14. A method of applying attachments to human teeth according to claim 1 further comprising: employing aligner manufacturer software to develop a patient treatment plan specifying desired types of said prefabricated attachments and desired placement locations of said prefabricated attachments; and employing digital mapping to facilitate placement of said prefabricated attachments to approximate the previously determined desired placement locations for said prefabricated attachments to be bonded onto a patient's teeth.

15. A method for applying attachments to human teeth comprising the steps of:
A. constructing a series of shapes of prefabricated attachments comprising a bioconcave base;

B. affixing said prefabricated attachments onto a patient's teeth in advance of developing dental impressions or digital scans of the patient's teeth;

C. developing dental impressions or scans of the patient's teeth and affixed prefabricated attachments;

D. forwarding said dental impressions or scans to an aligner manufacturer o determine the final shape and position of said prefabricated attachments on a patient's teeth and optimal force vector parameters corresponding to a prefabricated attachment delivery tray.

16. A method for applying attachments to human teeth according to claim 15 wherein said prefabricated attachments range in size from approximately 2 millimeters to 5 millimeters in width and length and 1 to 2 millimeters in depth.

17. A method for applying attachments to human teeth according to claim 15 wherein said prefabricated attachments incorporate various shapes comprising a quarter sphere, cuboid, triangular prisms, trapezium prisms or triangular based prisms.

18. A method for applying attachments to human teeth according to claim 15 wherein said bioconcave base of said prefabricated attachments comprises concavity approximating the contours of the patient's teeth intended to receive said prefabricated attachments to facilitate smooth positioning of said prefabricated attachments onto a patient's teeth by a clinician.

19. A method for applying attachments to human teeth according to claim 15 wherein the aligner manufacturer evaluates said dental impressions or one or more digital scans of the patient's teeth to determine whether previously applied prefabricated attachments accomplish desired tooth movement.

20. A method for applying attachments to human teeth according to claim 19 wherein the aligner manufacturer employs software reformulation to generate additional prefabricated attachments based on review of said dental impressions or said one or more digital scans to modify placement location of previously positioned prefabricated attachments in order to accomplish desired tooth movement and provide said additional prefabricated attachments to the clinician in said prefabricated attachment delivery tray.

21. An apparatus for applying prefabricated attachments to human teeth comprising:

(A) A retention register to facilitate transferring prefabricated attachments from a model of a patient's teeth onto the enamel surfaces of a patient's teeth; and (B) An etching stencil used in conjunction with said retention register to diminish the presence of excess bonding plastic on a patient's teeth after prefabricated attachments are placed onto a patient's teeth.

22. The apparatus of claim 21 wherein said retention register further comprises a plurality of retention legs moldably attached to said retention register to form at least one slide-lock channel to secure prefabricated attachments into attachment delivery trays.

23. The apparatus of clam 22 wherein said plurality of retention legs of said retention register are color coded to create a distinct junction between prefabricated attachments and said retention register to facilitate accurate removal of said retention register and corresponding said plurality of retention legs after prefabricated attachments are placed onto a patient's teeth.

24. The apparatus of claim 22 wherein a plurality of demarcation scribe lines disposed between prefabricated attachments and said plurality of retention legs of said retention register create a distinct junction between said prefabricated attachments and said retention register to facilitate accurate removal of said retention register and corresponding said plurality of retention legs after prefabricated attachments are placed onto a patient's teeth.

25. The apparatus of claim 22 wherein an undercut arch of said retention register is constructed with sufficient depth to create prevent prefabricated attachments from falling out of prefabricated attachment delivery trays during handling, and sufficient weight to facilitate accurate separation of said retention register and corresponding prefabricated attachments from prefabricated attachment delivery trays after prefabricated attachments are placed onto a patient's teeth.

26. The apparatus of claim 22 wherein said plurality of channels disposed on said plurality of retention legs of said retention register facilitate single direction positioning of said retention register and corresponding prefabricated attachment into prefabricated attachment delivery trays.

27. The apparatus of claim 21 wherein said retention register having said plurality of retention legs is fabricated into the facial surface of prefabricated attachments to facilitate fitting prefabricated attachments into corresponding delivery trays.

28. The apparatus of claim 21 wherein said etching stencil further comprises a plurality of openings to facilitate bonding adhesive application and a moldably disposed dam to control etchant flow during application of etching material to the enamel surfaces of a patient's teeth.

29. The apparatus of claim 28 wherein said moldably disposed dam of said etching stencil is designed to diminish the presence of excess bonding plastic on a patient's teeth after prefabricated attachments are placed onto a patient's teeth.

30. The apparatus of claim 28 wherein said plurality of openings of said etching stencil are fabricated using laser technology to ensure that said plurality of openings accurately approximate the intended location for placement onto a patient's teeth.

* * * * *